United States Patent [19]

Kydonieus et al.

[11] 4,272,520

[45] Jun. 9, 1981

[54] COMPOSITIONS COMPRISING N-TETRADECYL FORMATE AND THEIR USE IN CONTROLLING INSECTS

[75] Inventors: Agis F. Kydonieus, New York, N.Y.; Roger L. Kitterman, Tonopah, Ariz.

[73] Assignee: Herculite Products, Inc., New York, N.Y.

[21] Appl. No.: 27,329

[22] Filed: Apr. 5, 1979

[51] Int. Cl.³ .................................................. A01N 25/00
[52] U.S. Cl. .................................................... 424/84
[58] Field of Search .......................................... 424/84

[56] References Cited

U.S. PATENT DOCUMENTS

| | | | |
|---|---|---|---|
| 3,062,659 | 11/1962 | Hyson et al. | 426/312 |
| 3,866,349 | 2/1975 | Meijer et al. | 424/84 |
| 3,952,093 | 4/1976 | Roelofs et al. | 424/84 |
| 3,980,771 | 9/1976 | Meijer et al. | 424/84 |
| 4,042,681 | 8/1977 | Underhill et al. | 424/84 |
| 4,059,689 | 11/1977 | Struble et al. | 424/84 |

OTHER PUBLICATIONS

Beroza, Pest Management with Insect Sex Attractants and Other Behavior–Controlling Chemicals; ACS Symposium Series, 8/26/75.
Bierl et al.; J. Econ. Ent. pp. 211–216 vol. 67, No. 12 (1974).
Nature; vol. 220 11/09/68, pp. 600–601.

Primary Examiner—Allen J. Robinson
Attorney, Agent, or Firm—Sughrue, Rothwell, Mion, Zinn and Macpeak

[57] ABSTRACT

N-Tetradecyl formate has been found to be effective as a sex pheromone mimic for disrupting the reproductive cycle of insects, especially the Heliothis complex which includes *Heliothis zea* (corn earworm), *Heliothis virescens* (tobacco budworm), and *Heliothis armigera*. The compound and compositions containing the compound n-tetradecyl formate may be applied to crops which are subject to damage by such insects in any suitable manner, for example, in sprays, dusts and powders. Particularly effective compositions comprise polymeric particles or flakes containing n-tetradecyl formate. The particles or flakes may have an adhesive coating so that upon application the particles become attached to the upper leaves, stalks, etc. where the insects tend to be more concentrated.

5 Claims, 1 Drawing Figure

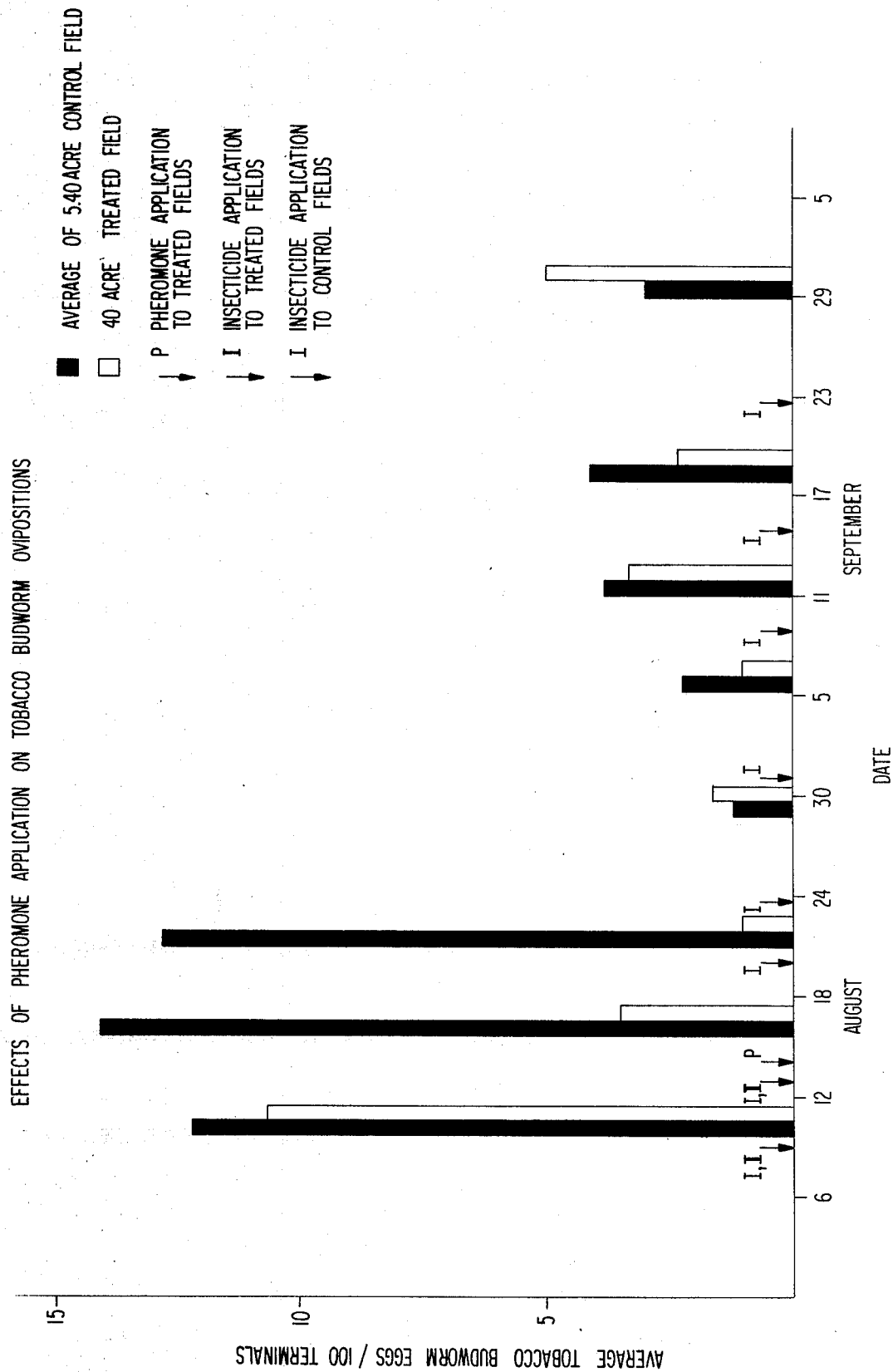

COMPOSITIONS COMPRISING N-TETRADECYL FORMATE AND THEIR USE IN CONTROLLING INSECTS

BACKGROUND OF THE INVENTION

1. Description of the Prior Art

In view of environmental problems arising from the widespread use of insecticides to control undesirable insects, attention has turned in recent years to other insect control techniques including the use of sex attractant pheromones for trapping insects or disrupting their reproductive cycle. Therefore, research has turned to the identification of the chemicals found in nature which are sex attractants for various insect species and to the commercial synthesis of such compounds and their mimics, i.e., compounds which imitate the sex attractant effect of the natural compounds although having a different chemical structure.

The Heliothis complex, such as, *Heliothis zea* (corn earworm), *Heliothis virescens* (tobacco budworm), and *Heliothis armigera* includes some of the pests most damaging to valuable agricultural in this country and other parts of the world.

Reserchers have determined that a combination of cis-9-tetradecenal and cis-11-hexadecenal is a sex attractant for males of the species *Heliothis virescens* and that a combination of cis-11-hexadecenal with several other components has similar attractant properties with respect to *Heliothis zea*. See U.S. Pat. No. 3,952,093, Roelofs et al, issued Apr. 20, 1976. See also Klem et al, Entomological Society of America presentation, Houston, Tex., Nov. 29, 1978. Other sex pheromones for other insect species bearing some chemical similarity to cis-9-tetradecenal and cis-11-hexadecenal are described in U.S. Pat. Nos. 3,866,349, Meijer et al, issued Feb. 18, 1975, 3,980,771, Meijer et al, issued Sept. 14, 1976, 4,042,681, Underhill, issued Aug. 16, 1977, and 4,059,689, Struble, issued Nov. 22, 1977.

The synthesis of the cis-9-tetradecenal and cis-11-hexadecenal sex attractants for *Heliothis virescens* and *Heliothis zea* as described in U.S. Pat. No. 3,952,093 is fairly complex and the chemicals are expensive. When released into the atmosphere of infested areas, these chemicals confuse males seeking females for mating thereby disrupting the mating of the insects.

2. Field of the Invention

Applicants have found surprisingly that an effective sex pheromone mimic for the Heliothis complex is provided by n-tetradecyl formate, $CH_3(CH_2)_{13}OCHO$, a relatively inexpensive chemical. Unlike the peromones of U.S. Pat. No. 3,952,093, n-tetradecyl formate has no double bonds at all in the carbon chain and would not be expected to behave as the sex pheromone mimic for the Heliothis species and to disrupt mating of the insects.

Accordingly the object of the present invention is to provide as an effective sex pheromone mimic for male moths of the Heliothis complex the compound n-tetradecyl formate and its compositions. A further object of the invention is to provide a method for controlling insects of the Heliothis complex by using n-tetradecyl formate and its formulations to disrupt the reproductive cycle of the species.

SUMMARY OF THE INVENTION

According to this invention applicants have discovered that n-tetradecyl formate is an effective mimic of the sex attractant pheromone of the Heliothis complex, including *Heliothis virescens* (tobacco budworm), *Heliothis zea* (corn earworm), and *Heliothis armigera*. The compound is useful to confuse the male species of the Heliothis complex and therefore can be employed in methods for disrupting mating of the insects. Particularly useful formulations have been developed for utilizing n-tetradecyl formate in insect control. The compositions comprise polymeric controlled release dispensers for the n-tetradecyl formate; the dispensers may take the form of particles or flakes of polymer in which the n-tetradecyl formate is soluble or dispersible and from which it is releasable over a period of time. Greater effectiveness is achieved with such compositions if the particles or flakes are provided with an adhesive coating so that upon being sprayed or otherwise distributed over a crop containing area a substantial portion of the particles or flakes will adhere to the upper or terminal parts of the plants where the insect concentration is apt to be greatest.

DESCRIPTION OF THE DRAWING

The single FIGURE of the drawing is a histogram which compares the results of insecticide spraying of tobacco budworm infested crops with the treatment of a similar field with n-tetradecyl formate.

DETAILED DESCRIPTION OF THE INVENTION

The sex pheromone mimic of the present invention is n-tetradecyl formate, $CH_3(CH_2)_{13}OCHO$. The compound may be prepared by synthetic procedures well known in the art of organic synthesis. One suitable method for preparation is set forth in the following example.

EXAMPLE 1

Preparation of n-tetradecyl formate

The preparation of n-tetradecyl formate is carried out as follows:

Reflux for 6 hours the mixture of 25 grams tetradecyl alcohol, 25 grams 97% formic acid and 125 ml dry benzene with a Dean-Starke apparatus to remove water continuously as formed. Allow the mixture to cool and add 250 ml ether and 250 ml water. After shaking in a separatory funnel, wash organic layer successively with cold water, 5% sodium bicarbonate solution, and saturated aqueous sodium chloride. Dry over sodium sulfate, filter and concentrate solution; and then distill. Bp 102–108/0.25 mm. The yield of product was 78%.

The sex pheromone mimic n-tetradecyl formate may be used in insect control in any suitable form and in any effective procedure, including but not limited to disruption of mating. For example, n-tetradecyl formate may be deployed in liquid or solid (dusts, powders, particles, flakes, tapes, etc.) form as by spraying or otherwise deploying the liquid or solid compositions from planes or from ground vehicles or backpacks. To prolong the effective life of the compound it has been found to be useful to incorporate the compound in a controlled release polymeric substrate, such as, a lower polyolefin, e.g., polyethylene, -propylene, -butylene, etc., polyvinyl chloride, ethylene-vinyl acetate copolymers, etc. The most suitable polymeric substrates will generally be thermoplastics into which the n-tetradecyl formate may be blended by hot milling. Another procedure for incorporating the compound into polymeric carriers includes forming a plastisol of polymer, such as a conventional PVC plastisol, and dispersing the n-tetradecyl formate in the plastisol. The plastisol can then be solidified and used, per se, or it may be incorporated as a lamina in a multilayer dispenser prepared generally in accordance with procedures as set forth in U.S. Pat. Nos. 3,705,938. In accordance with the procedure described in that patent, the active agent n-tetradecyl formate may be incorporated in a vinyl plastisol adhesive; the adhesive is then used to laminate two plies of polyvinyl chloride sheeting each of a few mils thickness under heat and pressure to produce a three layer product. The n-tetradecyl formate migrates to the surface of the composite.

Preferred compositions of the invention are particles or flakes, about $\frac{1}{8}'' \times \frac{1}{8}''$ and a few mils in thickness formed from PVC into which n-tetradecyl formate has been incorporated, either by the above described laminating procedure or by blending into a PVC melt prior to extrusion. The details of preparation of the preferred compositions are set forth in Example 2.

EXAMPLE 2

Preparation of Polymeric Controlled Release Particles Containing n-Tetradecyl Formate Flakes of PVC containing n-tetradecyl formate useful in the present invention were prepared as follows:
1. Starting Materials
   (a) PVC, plasticized with 23% of dioctylphthalate plasticizer
   (b) n-tetradecyl formate
2. Blending Procedure The starting materials were placed in a low-shear, propeller-type rotary blender and mixed for 15 min. at room temperature at which point the n-tetradecyl formate was substantially (homogenously dispersed or blended) in the PVC. The amounts were proportioned to produce a blend containing 30% n-tetradecyl formate, 23% dioctyl phosphate, and the balance PVC (plus 1% CdBaZn phosphide stabilizer).

3. Laminate Fabrication

The blend from Step 2, above, was coated uniformly (3 ozs. per sq yd) onto a 2 ml vinyl film and then a second vinyl film was laid on top of the uniformly coated blend. The three-layered structure was heated for 15 seconds to 300° F., thus curing the blend and laminating the structure together. The final concentration of n-tetradecyl formate in the final product was 25 mg/sq.in. or about 15% by weight.

The resulting laminated film is useful per se, if cut into strips or the like and strung throughout fields to achieve a mating disruption effect. It is believed however that the most effective method to disrupt the reproductive cycle of the Heliothis complex is to dispense compound-containing particles or flakes substantially uniformly over the crop growing area subject to infestation by the Heliothis complex.

4. Flake Formation

The method for forming flakes and the precise size and composition of the flakes or particles is not critical but naturally the flake should be able to hold a sufficient amount of n-tetradecyl formate so that the flake serves as a confusant site over a period of time, preferably several weeks or more, so as effectively to interrupt the reproductive cycle of the Heliothis complex species by confusing the males during the mating period.

It has been found that suitable flake-like polymeric dispensers can be formed from the sheet material of step 3 above, by freezing and milling the sheet or film material. Freezing is accomplished by introducing into a grinder, commonly used to grind polymeric materials (such as those manufactured by Cumberland), liquid nitrogen at the same time that the sheet is introduced into the grinder. A sieve below the grinder allows a particular size of flake to pass through. Depending on the amount of liquid nitrogen and the screen used, smaller or bigger flakes can be obtained.

A second method that gives uniform flakes is a "dicer". Such equipment (also produced by Cumberland) feeds the sheet directly into the knifed portion of the dicer so that exactly $\frac{1}{8}'' \times \frac{1}{8}''$ (or different sizes, as desired) can be obtained. A flake size averaging about $\frac{1}{8}'' \times 150'' \times 7$ mils thick was obtained using "dicer" equipment.

5. Coating of Flakes With Adhesive

The resulting flakes can be used, per se, by any suitable mode of application to threatened crops. Experience has shown, however, that the full effect of the n-tetradecyl formate disruptant is not realized if the flakes are sprayed on the crops under conditions such that they can readily fall to the ground due to gravity alone or aided by wind and/or rain. Better results are obtained by applying the flakes so that at least some adhere to the terminal portions, i.e., the upper leaves, stalks, and fruit of the crop in question. It has been found that this can be accomplished by applying a suitable adhesive or tackifier (sticker) to the flakes such that at least a portion of them adhere to the upper, terminal portions of the plants making up the crop which is to be treated.

Any suitable adhesive may be used, it being necessary only that the adhesive be capable of adhering the n-tetradecyl formate containing flakes or particles to the plant in question and that the adhesive not interfere in any substantial way with the disruptant activity of the compound. Suitable adhesives include, without limitation, polybutene, and some acrylic and vinyl acetate emulsions.

In the preferred embodiment, the adhesive is applied to the flakes obtained in step 4, above, mixing 50% by volume polybutene adhesive and 50% flakes. No special equipment or conditions of mixing are required as the two components are easily blended by simply stirring.

As noted above, the n-tetradecyl formate can be used, per se, or in any suitable composition to confuse mating, thus interrupting the reproductive cycle, or otherwise to control the insects' behavior.

The most effective method noted to date for the utilization of n-tetradecyl formate to control the Heliothis complex comprises uniformly spraying the adhesive coated flakes of step 5, above, over the crop-containing area so that at least some of the flakes adhere to the terminal portions of the plants to interrupt the reproductive cycle by confusing the males during the mating period. The composition may be sprayed from an airplane in accordance with known practice using a screw metering device and a spinning disc generator which effectively breaks up clumps or agglomerates and deploys a spray, predominantly of discrete flakes, over the area to be treated. The method for utilizing the composition of the invention for insect control by the confusion technique has been field tested and is described in Example 3.

EXAMPLE 3

Use of Adhesive Coated Polymeric Flakes Containing n-Tetradecyl Formate to Control the Heliothis Complex by Mating Confusion The compositions as finally prepared in step 5 of Example 2 were field tested to determine efficacy in controlling species of the Heliothis complex on cotton crops.

(a) Materials

Approximately 60 ounces of $\frac{1}{8}'' \times \frac{1}{8}'' \times 7$ mils thick flakes prepared as described in Example 2, step 5, above, were used for each spraying of a single plot. As noted in Example 2 this was a 50%/50% by volume blend of flakes and polybutene adhesive.

(b) Test Fields

Six 40 acre plots planted with cotton were used in the test, five being used as controls and the sixth being used to determine the relative efficacy of the n-tetradecyl formate containing composition of (a), above, in comparison with standard insecticides used commercially for tobacco budworm control.

(c) Test Procedure

The five control plots and one test plot were sprayed on August 13 with 1.5 methyl parathion and 0.34 pt. Fundal, insecticides conventionally used to combat the tobacco budworm. Thereafter, the control plots were sprayed at approximately equal intervals with similar concentrations of insecticides and on six other occasions at a few days interval up to September 23. As noted, the test plot to be treated with the n-tetradecyl formate material was also sprayed once on August 13, so both the five control fields and the field to be treated with the compound of the invention received the same initial treatment.

On August 14, the test plot was also treated with n-tetradecyl formate as follows:

(a) rate of active mimic/acre—5 grams n-tetradecyl formate/acre
(b) rate of flakes/acre—20,000 flakes (approx. $\frac{1}{8}'' \times \frac{1}{8}'' \times 7$ mils)/acre (prepared as in Example 2, step 5)
(c) application—uniform spraying from airplane of composition as described in a) above.

The results of this comparative testing are shown in the histogram in the drawing. The bars indicate the average tobacco budworm egg count/100 cotton plant terminals; the solid bars indicate the average egg count in the control fields sprayed periodically with conventional insecticides, while the open bars indicate the egg count in the test field, sprayed once with insecticide and then treated with the sex phermone mimic of the inveition, n-tetradecyl formate. It will be seen that the confusion technique using the n-tetradecyl formate of the invention was significantly more effective than the insecticide in controlling the tobacco budworm on the cotton crop. One anomaly appears on about August 30 where after four insecticide sprayings, the average count of tobacco budworm eggs/100 terminals was slightly lower for the control field as compared with the n-tetradecyl formate treated field, but the difference is slight and may be within experimental error. Even so it is significant to note that insect control with one treatment of the pheromone mimic of the invention is comparable to what is achieved on the control fields after four sprayings of insecticide.

Thereafter the n-tetradecyl formate treated field again shows superiority to the average of the control fields in three subsequent surveys. Only in the last measurement on about September 29 did the treated field show a higher count of tobacco budworm eggs than the average of the untreated fields and by then the n-tetradecyl formate in the polymeric dispenser flakes had been substantially dissipated. Also, the count in the control fields had also begun to rise despite seven applications of insecticide.

What is claimed is:

1. A method for controlling insects of the Heliothis complex species by disruption of the reproductive cycle of said insects comprising substantially uniformly distributing, over an area containing crops which are subject to infestation by said insects, n-tetradecyl formate, the amount of n-tetradecyl formate being sufficient to impede moths in finding female moths thereby interrupting mating of said insects.

2. The method of claim 1, wherein said n-tetradecyl formate is incorporated in solid particles of material.

3. The method of claim 2, wherein said particles have on at least a portion of their surfaces an adhesive capable of causing at least some of said particles to adhere to the terminal portions of said crops.

4. The method of claim 1, wherein said n-tetradecyl formate is incorporated in solid particles of a polymeric material from which the n-tetradecyl formate is released to the atmosphere.

5. The method of claim 4, wherein said particles have on at least a portion of their surfaces an adhesive capable of causing at least some of said particles to adhere to the terminal portions of said crops.

* * * * *